(12) United States Patent
Chung et al.

(10) Patent No.: US 7,663,357 B2
(45) Date of Patent: Feb. 16, 2010

(54) SIGNAL READOUT CIRCUIT FOR AMPEROMETRIC SENSOR

(75) Inventors: Wen-Yaw Chung, Taoyuan Hsien (TW); Tsai-Tseng Kuo, Dayuan Township, Taoyuan County (TW); Ying-Hsian Wang, Tucheng (TW); Dorota Genowefa Pijanowska, Nieporet (PL); Wladyslaw Torbicz, Warsaw (PL)

(73) Assignee: Chung Yuan Christian University, Chung Li (TW)

( * ) Notice: Subject to any disclaimer, the term of this patent is extended or adjusted under 35 U.S.C. 154(b) by 309 days.

(21) Appl. No.: 11/945,365

(22) Filed: Nov. 27, 2007

(65) Prior Publication Data

US 2008/0169800 A1    Jul. 17, 2008

(30) Foreign Application Priority Data

Jan. 17, 2007    (TW) .............................. 96101770 A (51) Int. Cl.
*G01N 27/00* (2006.01)
*G01N 27/404* (2006.01)
(52) U.S. Cl. ................. 324/71.1; 324/425; 205/775
(58) Field of Classification Search ................ 324/71.1, 324/425; 205/775
See application file for complete search history.

(56) References Cited

U.S. PATENT DOCUMENTS 5,202,637 A * 4/1993 Jones .......................... 324/425
6,428,684 B1 * 8/2002 Warburton ................... 205/775

OTHER PUBLICATIONS

Integrated VLSI potentiostat for cyclic voltammetry in electrolytic reactions, Harpreet S. Narula et al., Proceedings of the IEEE Computer Society Annual Symposium on VLSI Emerging Trends in VLSI System Design (ISVLSI' 04), 2004.
Integrating Data Converters for Picoampere Currents From Electrochemical Transducers, Madalina Breten et al., ISCAS 2000—IEEE International Symposium on Circuits and Systems, p. 709-712, May 28-31, 2000.
A CMOS Potentiostat for Amperometric Chemical Sensors, Robin F. B. Turner et al., IEEE Journal of Solid-State Circuits, vol. SC-22, No. 3, p. 473-478, Jun. 1987.

* cited by examiner

*Primary Examiner*—Vincent Q Nguyen
(74) *Attorney, Agent, or Firm*—Rabin & Berdo, P.C.

(57) ABSTRACT

A signal readout circuit for amperometric sensor for reading a readout signal of a sensor includes an amplifier, a first transistor, a second transistor, and a first resistor. A negative input end of the amplifier receives an input voltage, and a positive input end of the amplifier is connected to a reference electrode of the sensor. Gates of the first transistor and the second transistor are connected to an output end of the amplifier, a drain of the first transistor is connected to a counter electrode of the sensor, and a drain of the second transistor is connected to the first resistor.

16 Claims, 6 Drawing Sheets

SIGNAL READOUT CIRCUIT FOR AMPEROMETRIC SENSOR

CROSS-REFERENCE TO RELATED APPLICATIONS

This non-provisional application claims priority under 35 U.S.C. § 119(a) on Patent Application No(s). 096101770 filed in Taiwan, R.O.C. on Jan. 17, 2007, the entire contents of which are hereby incorporated by reference.

BACKGROUND OF THE INVENTION

1. Field of Invention

The present invention relates to a readout circuit more particularly to a signal readout circuit for an amperometric sensor.

2. Related Art

A blood glucose meter is used as an index indicating daily health status for ordinary people, and also used as a device for evaluating the prevention and curing effects for people in high risk groups or already being sick. Recently, the most common inspection method is conducted by an electrochemical-based amperometric sensor.

Figure 1:
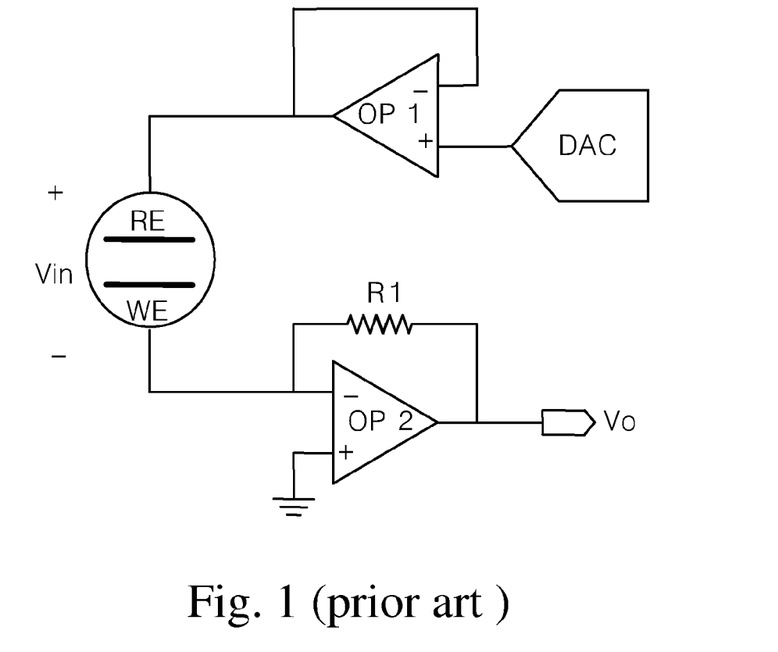
FIG. 1 is a signal readout circuit for an amperometric sensor according to the prior art.

The amperometric sensor is generally divided into dual-electrode sensor and tri-electrode sensor. FIG. 1 is a readout circuit for a common dual-electrode amperometric sensor, which uses the virtual short circuit characteristic of OP2 to pass the voltage of the working electrode to the ground, and uses OP1 as a voltage follower to provide the voltage input.

Moreover, Turner, R. F. B.; Harrison, D. J.; Baltes, H. P et al. also disclosed a readout circuit for a dual-electrode amperometric sensor in "A CMOS potentiostat for amperometric chemical sensors"; IEEE Journal of Solid-State Circuits; Volume 22, Issue 3, June 1987 Page(s): 473-478. In addition, Breten, M.; Lehmann, T.; Braun, E. et al. disclosed a readout circuit for a dual-electrode amperometric sensor in "Integrating data converters for picoampere currents from electrochemical transducers"; ISCAS 2000 IEEE International Symposium on Circuit and system; Volume 5, 28-31 May 2000 Page(s): 709-712.

Narula, H. S.; Harris, J. G. et al. published similar circuits in "Integrated VLSI potentiostat for cyclic voltammetry in electrolytic reactions"; IEEE Computer society Annual Symposium on VLSI; 19-20 Feb. 2004 Page(s): 268-270.

The dual-electrode sensing architecture has some problems, and the main disadvantage lies in that when the solution is in reaction, anion moves towards anode and cation moves towards cathode, such that the charged ions are attached to the surface of the reference electrode, so as to produce a concentration polarization phenomenon which further affects the electric potential changes in the solution and is more obvious when the measured current is larger than 10 uA.

Figure 2:
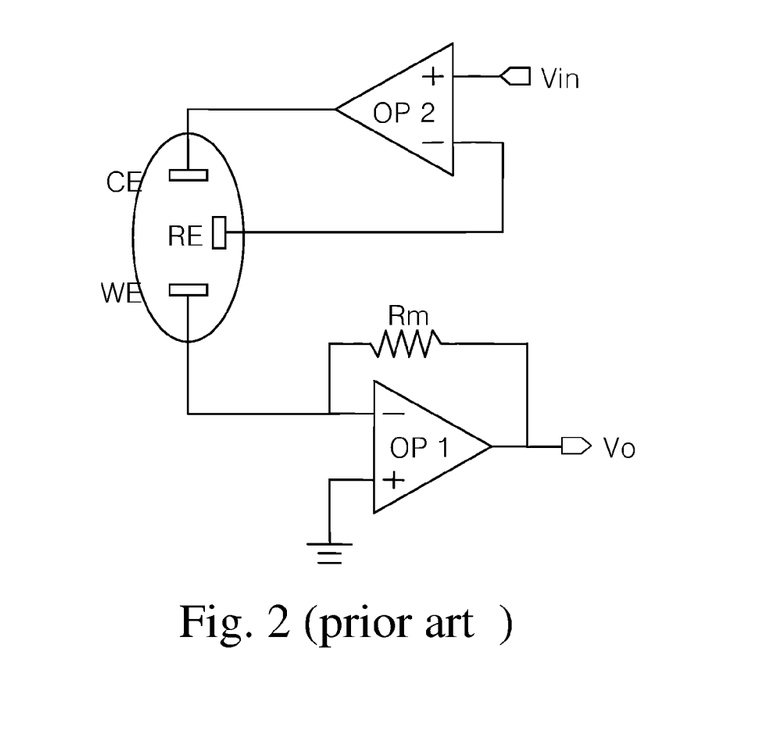
FIG. 2 is another signal readout circuit for an amperometric sensor according to the prior art.

FIG. 2 shows another constant potential instrument used in a readout circuit for a tri-electrode amperometric sensor. The circuit is characterized in an amplifier OP1 which causes that the working electrode must be grounded. Thus, when the voltage across the electrode is to be detected, it is only necessary to measure a voltage on the reference electrode, and perform a synergism on the measured voltage and an input voltage (Vin). Then, the result is amplified by an amplifier OP2, and fed back to control a counter electrode (CE). The current signal of the reaction current is converted into a voltage signal after passing through a resistor Rm.

In fact, the voltage on working electrode (WE) is not virtually grounded, when the frequency increases, the voltage on the WE will increase accordingly. This characteristic is similar to inductance, and the inductance is easy to produce resonance with the double-layer capacitor between electrodes, thus causing the whole circuit to be unstable.

In view of the above various limitations and changes of era, the requirements on the effectiveness of implementing medical treatments on medical spots are rather urgent. Under such circumstance, the detection system having small equipments, convenient operations, portability, and real time capability gradually becomes a trend, so the electrochemical analysis method with developing potential of meeting the above requirements is highly favored recently.

SUMMARY OF THE INVENTION

Accordingly, the present invention discloses a signal readout circuit for an amperometric sensor, so as to solve the technical problems of the prior art.

A signal readout circuit for an amperometric sensor disclosed in an embodiment of the present invention is used for reading a readout signal of a sensor. The readout circuit includes an amplifier, a first transistor, a second transistor, and a first resistor. A negative input end of the amplifier receives an input voltage and a positive input end of the amplifier is connected to a reference electrode of the sensor. Gates of the first transistor and the second transistor are connected to an output end of the amplifier, a drain of the first transistor is connected to a counter electrode of the sensor, and a drain of the second transistor is connected to the first resistor.

A signal readout circuit for an amperometric sensor disclosed in another embodiment of the present invention includes an amplifier, a first transistor, a second transistor, a third transistor, a fourth transistor, and a first resistor. A negative input end of the amplifier receives an input voltage, and a positive input end of the amplifier is connected to a reference electrode of the sensor. Gates of the first transistor and the second transistor are connected to an output end of the amplifier, sources of the third transistor and the fourth transistor are connected to drains of the first transistor and the second transistor respectively, a drain of the third transistor is connected to a counter electrode of the sensor, and a drain of the fourth transistor is connected to the first resistor. Gates of the third transistor and the fourth transistor are connected to a common constant bias.

In modern society, people are paying more and more attention to health, and patients suffering from certain diseases have to monitor physiological parameters, such as the blood sugar and uric acid, in daily life at any time. Therefore, driving circuits with low power consumption for biomedical sensors are becoming more and more important to meet the requirements of portable devices. The present invention uses an electrochemical measuring method to compensate the defects of the conventional color display method, and takes advantage of the characteristics of biological sensors to establish a readout signal for an amperometric sensor with low power consumption.

The above description of the content of the present invention and the following illustration of the embodiments are intended to demonstrate and explain the spirit and principle of the present invention and to provide further explanations of the claims of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus is not limitative of the present invention, and wherein.

DETAILED DESCRIPTION OF THE INVENTION

The detailed features and advantages of the present invention will be described in detail in the following embodiments. Those skilled in the arts can easily understand and implement the content of the present invention. Furthermore, the relative objectives and advantages of the present invention are apparent to those skilled in the arts with reference to the content disclosed in the specification, claims, and drawings.

Figure 3:
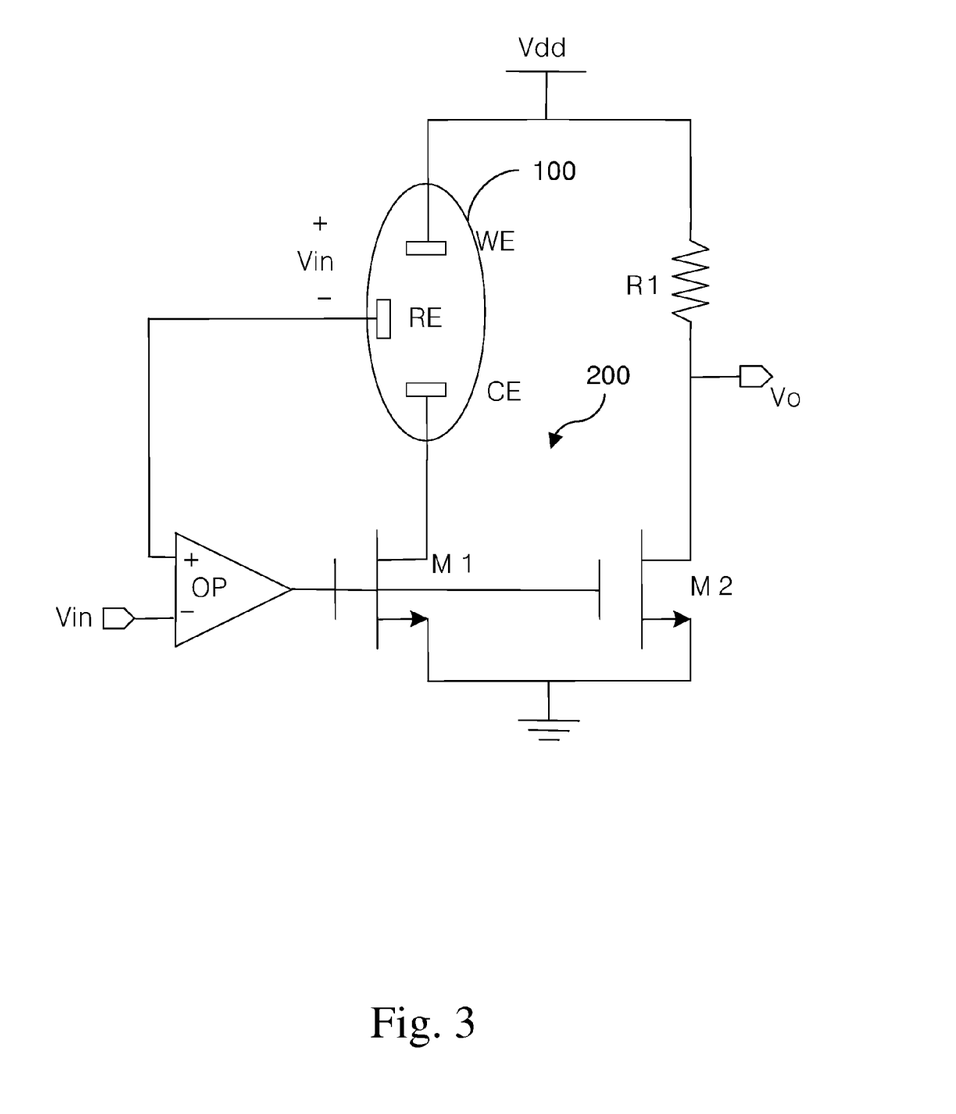
FIG. 3 is a signal readout circuit for an amperometric sensor according to one embodiment of the present invention.

In the blood sugar sensing mechanism, electrons move from the solution to the working electrode, i.e., the reaction of the solution near the working electrode is oxidation. Therefore, the current enters the solution from the working electrode, and flows out from the counter electrode. By detecting the oxidation current of the solution near the working electrode, the glucose concentration in the reaction can be determined. FIG. 3 is a signal readout circuit for an amperometric sensor disclosed by the present invention, which is a readout circuit designed for the oxidation of the solution near the working electrode.

As shown in FIG. 3, the signal readout circuit includes a sensor 100 and a readout circuit 200. The sensor 100 includes a working electrode WE, a reference electrode RE, and a counter electrode CE. The readout circuit 200 includes an amplifier OP, a first transistor M1, a second transistor M2, and a first resistor R1. A negative input end of the amplifier OP receives an input voltage Vin, a positive input end of the amplifier is connected to the reference electrode RE of the sensor 100, an output end of the amplifier OP is connected to gates of the first transistor M1 and the second transistor M2, and sources of the first transistor M1 and the second transistor M2 are connected to a ground terminal. A drain of the first transistor M1 is connected to the counter electrode CE of the sensor 100, and a drain of the second transistor M2 is connected to the first resistor R1. The output voltage Vo sensed by the sensor 100 is output from the drain of the second transistor M2.

Figure 4:
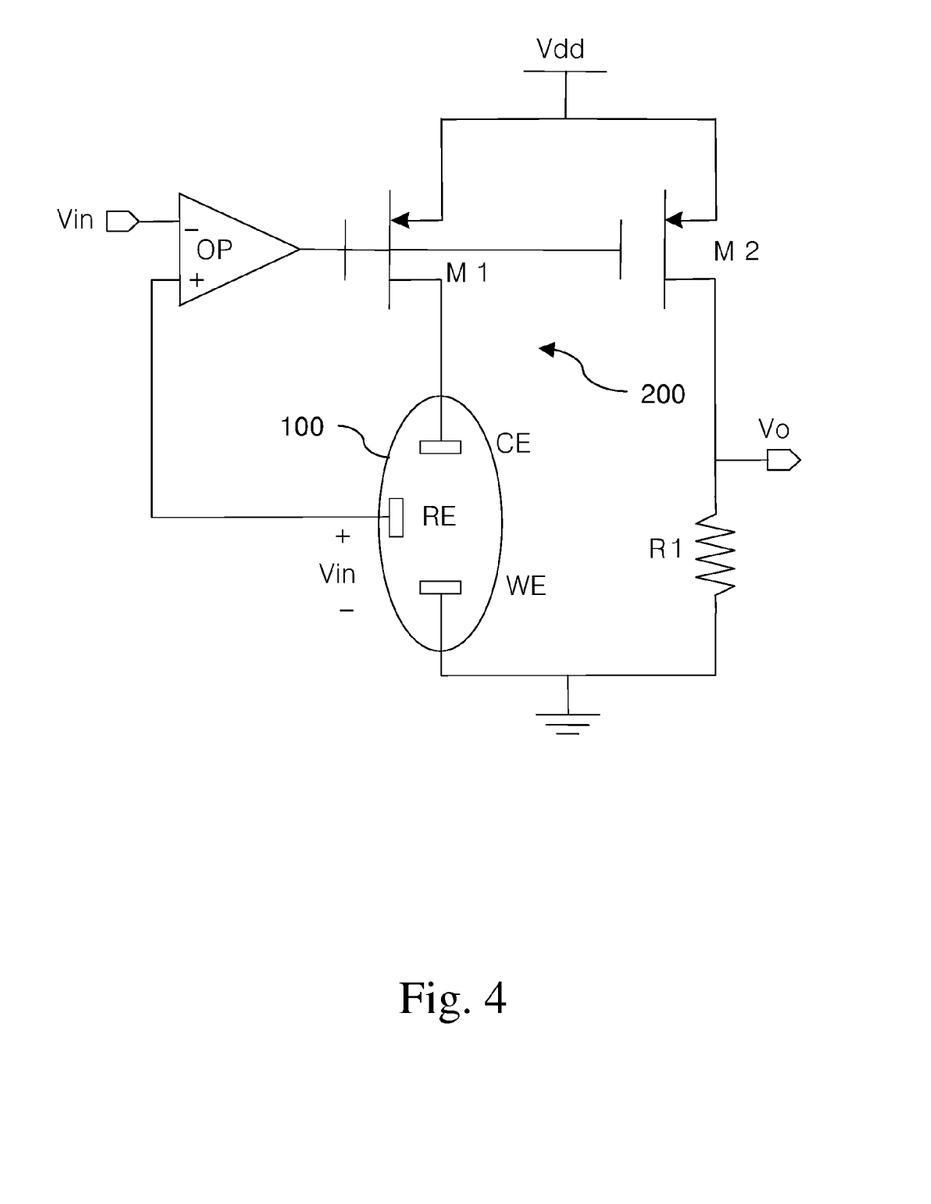
FIG. 4 is a signal readout circuit for an amperometric sensor according to another embodiment of the present invention.

FIG. 4 is a signal readout circuit for an amperometric sensor according to another embodiment of the present invention, which is designed for the reduction of the solution near the working electrode. The signal readout circuit includes a sensor 100 and a readout circuit 200. The sensor 100 includes a working electrode WE, a reference electrode RE, and a counter electrode CE. The readout circuit 200 includes an amplifier OP, a first transistor M1, a second transistor M2, and a first resistor R1. A negative input end of the amplifier OP receives an input voltage Vin, a positive input end is connected to the reference electrode RE of the sensor 100, an output end of the amplifier OP1 is connected to gates of the first transistor M1 and the second transistor M2, and sources of the first transistor M1 and the second transistor M2 are connected to a power source Vdd. A drain of the first transistor M1 is connected to the counter electrode CE of the sensor 100, and a drain of the second transistor M2 is connected to the first resistor R1. The output voltage Vo sensed by the sensor 100 is output from the drain of the second transistor M2.

In an embodiment of the present invention, the amplifier OP is an operational transconductance amplifier. The amplifier OP serves as an error amplifier, for detecting the voltage on the reference electrode RE and comparing the detected voltage with an input voltage Vin, and controlling the magnitude of current flowing through the first transistor M1, so as to regulate the voltage. Moreover, another advantage of this circuit architecture is that the second transistor M2 only needs to copy the current of the first transistor M1 when reading out the signal, and the first resistor R1 then converts the current signal into a voltage signal.

According to the above embodiments, the input voltage Vin must be taken into consideration. In the embodiment of FIG. 3, the working electrode of the sensor 100 is connected to a voltage source, so a reference voltage relative to the voltage source is needed to serve as the input voltage. In the embodiment of FIG. 4, the working electrode of the sensor 100 is grounded, so a reference voltage relative to the ground is needed to serve as the input voltage.

In the embodiments of FIGS. 3 and 4, the element width/length ratio (W/L) of the first transistor M1 and the second transistor M2 is the same or is at a specific proportion.

Figure 5:
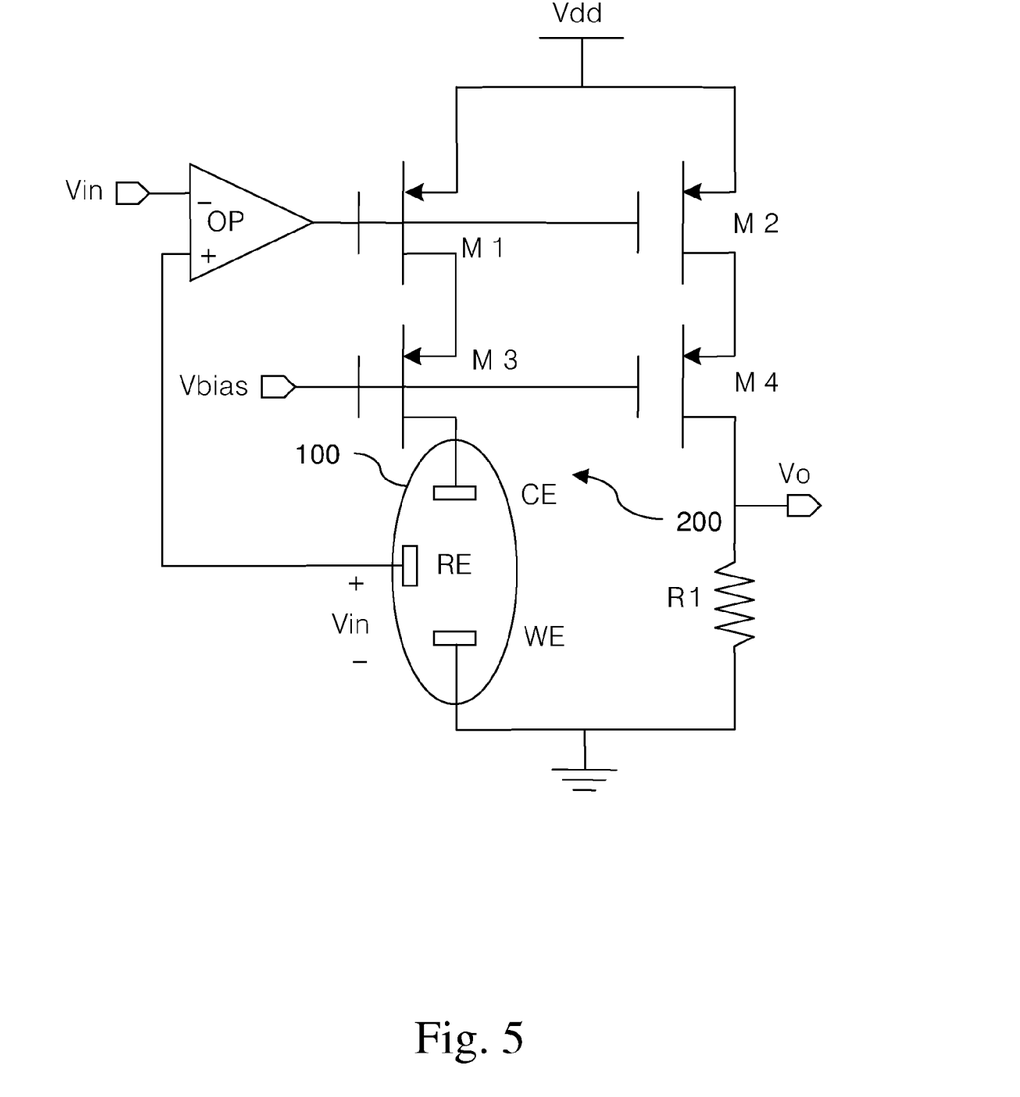
FIG. 5 is a signal readout circuit for an amperometric sensor according to still another embodiment of the present invention.

FIG. 5 is a signal readout circuit for an amperometric sensor according to still another embodiment of the present invention, which is a readout circuit designed for the reduction of the solution near the working electrode. The difference between the embodiments of FIGS. 4 and 5 is that the embodiment of FIG. 5 uses a stacked current mirror.

As shown in FIG. 5, the signal readout circuit includes a sensor 100 and a readout circuit 200. The sensor 100 includes a working electrode WE, a reference electrode RE, and a counter electrode CE. The readout circuit 200 includes an amplifier OP, a first transistor M1, a second transistor M2, a third transistor M3, a fourth transistor M4, and a first resistor R1. A negative input end of the amplifier OP receives an input voltage Vin, a positive input end is connected to the reference electrode RE of the sensor 100, an output end of the amplifier OP is connected to gates of the first transistor M1 and the second transistor M2, and sources of the first transistor M1 and the second transistor M2 are connected to a power source Vdd. Drains of the first transistor M1 and the second transistor M2 are connected to sources of the third transistor M3 and the fourth transistor M4 respectively. A drain of the third transistor M3 is connected to the counter electrode CE of the sensor 100, and a drain of the fourth transistor M4 is connected to the first resistor R1. Gates of the third transistor and the fourth transistor are connected to a common constant bias Vbias. The output voltage Vo sensed by the sensor 100 is output from the drain of the fourth transistor M4.

Figure 6:
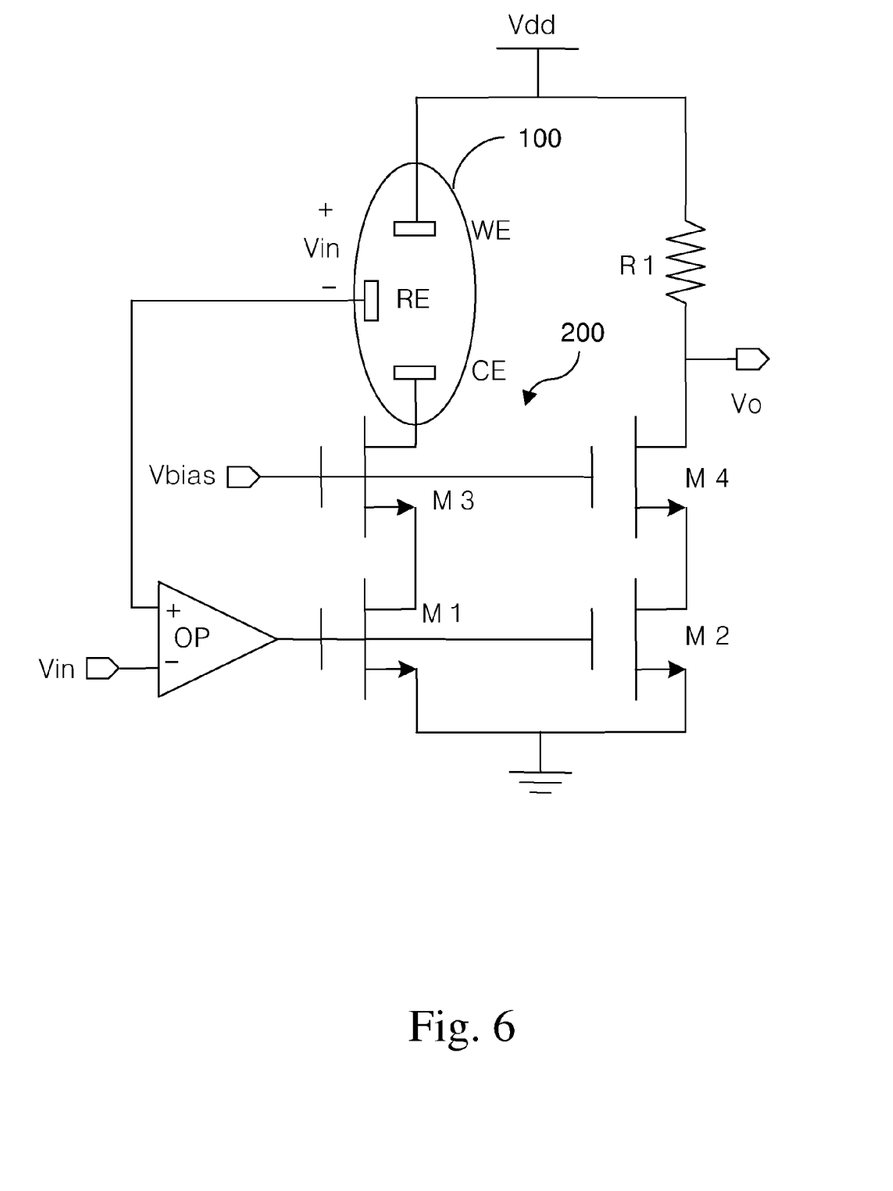
FIG. 6 is a signal readout circuit for an amperometric sensor according to yet another embodiment of the present invention.

FIG. 6 is a signal readout circuit for an amperometric sensor according to yet another embodiment of the present invention, which is a readout circuit designed for the oxidation of the solution near the working electrode. The difference between the embodiments of FIGS. 3 and 6 is that the embodiment of FIG. 6 uses a stacked current mirror.

As shown in FIG. 6, the signal readout circuit includes a sensor 100 and a readout circuit 200. The sensor 100 includes a working electrode WE, a reference electrode RE, and a counter electrode CE. The readout circuit 200 includes an amplifier OP, a first transistor M1, a second transistor M2, a third transistor M3, a fourth transistor M4, and a first resistor R1. A negative input end of the amplifier OP receives an input voltage Vin, a positive input end of the amplifier OP is connected to the reference electrode RE of the sensor 100, an output end of the amplifier OP is connected to gates of the first transistor M1 and the second transistor M2, and sources of the first transistor M1 and the second transistor M2 are connected to a ground terminal. Drains of the first transistor M1 and the second transistor M2 are connected to sources of the third transistor M3 and the fourth transistor M4 respectively. A drain of the third transistor M3 is connected to the counter electrode CE of the sensor 100, and a drain of the fourth transistor M4 is connected to the first resistor R1. Gates of the third transistor and the fourth transistor are connected to a common constant bias Vbias. The output voltage Vo sensed by the sensor 100 is output from the drain of the fourth transistor M4.

In the embodiments of FIGS. 5 and 6, a stacked current mirror is used, and a constant bias Vbias is applied to force the voltage Vds1 between the drain and the source of the first transistor M1 to be close to the voltage Vds2 between the drain and the source of the second transistor M2. Moreover, the influence of the channel length modulation effect is reduced, so as to improve the accuracy of the output current. However, the swing of the output voltage is relatively low.

Figure 7:
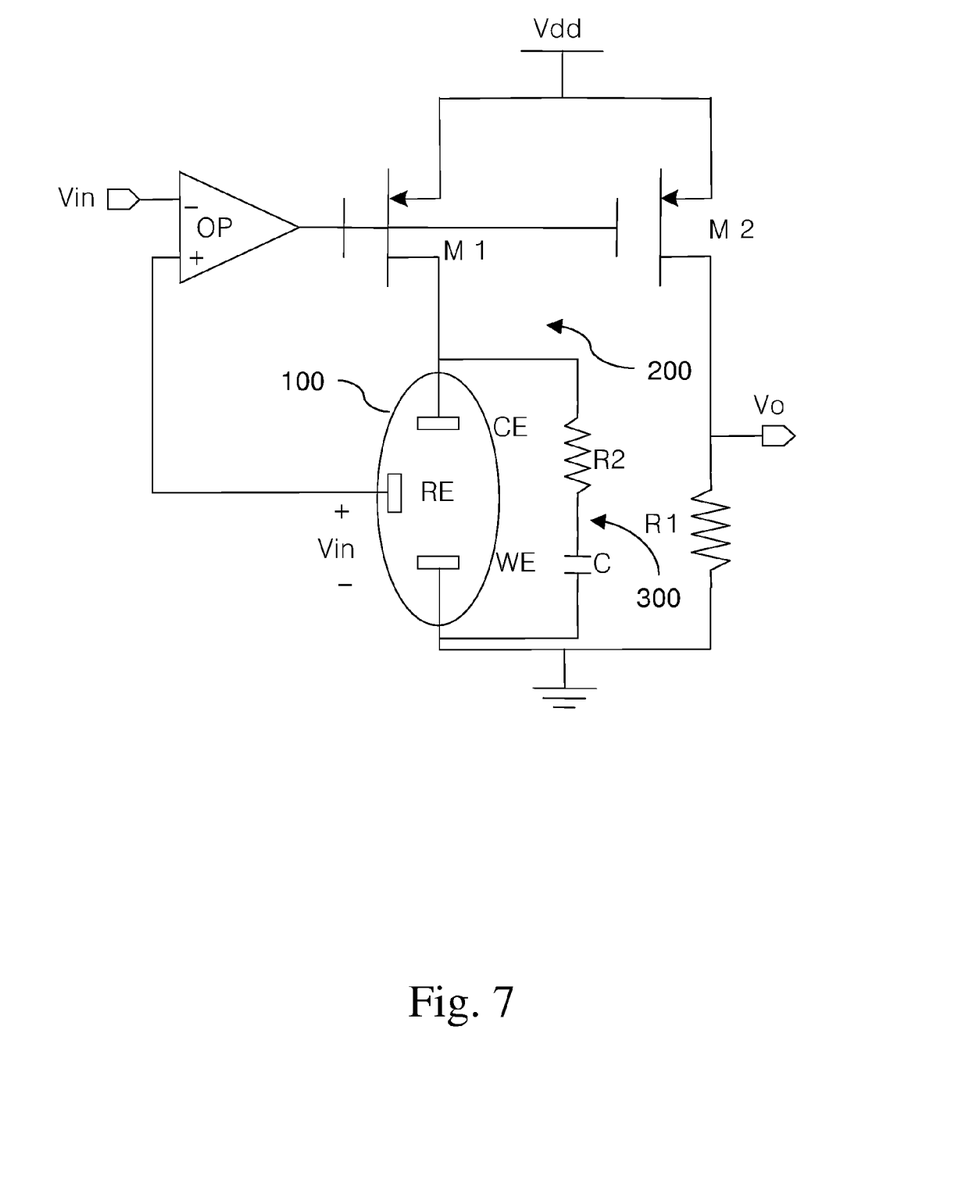
FIG. 7 is a signal readout circuit for an amperometric sensor according to further embodiment of the present invention.

FIG. 7 is a signal readout circuit for an amperometric sensor according to further embodiment of the present invention, which has an additional compensation circuit 300 connected in parallel with the sensor 100, so as to improve the stability of the readout circuit. The compensation circuit is composed of a capacitor and a second resistor connected in series. The compensation circuit is also applicable to the embodiments of FIGS. 3 to 6.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A signal readout circuit for amperometric sensor, for reading out a readout signal of a sensor, wherein the sensor has a working electrode, a reference electrode, and a counter electrode, the readout circuit comprising:
    an amplifier, having a positive input end, a negative input end, and an output end, wherein the negative input end receives an input voltage, and the positive input end is connected to the reference electrode of the sensor;
    a first transistor and a second transistor, each having a gate, a drain, and a source, wherein the gates of the first transistor and the second transistor are connected to the output end of the amplifier, and the gate of the first transistor is connected to the counter electrode of the sensor; and
    a first resistor, connected to the drain of the second transistor.

2. The signal readout circuit for amperometric sensor as claimed in claim 1, wherein the amplifier is an operational transconductance amplifier.

3. The signal readout circuit for amperometric sensor as claimed in claim 1, wherein the sources of the first transistor and the second transistor are connected to a power source, and a working electrode of the sensor is connected to a ground terminal.

4. The signal readout circuit for amperometric sensor as claimed in claim 3, further comprising a compensation circuit connected in parallel with the sensor.

5. The signal readout circuit for amperometric sensor as claimed in claim 4, wherein the compensation circuit comprises a second resistor and a capacitor connected in series.

6. The signal readout circuit for amperometric sensor as claimed in claim 1, wherein the sources of the first transistor and the second transistor are connected to a ground terminal, and the working electrode of the sensor is connected to a power source.

7. The signal readout circuit for an amperometric sensor as claimed in claim 6, further comprising a compensation circuit connected in parallel with the sensor.

8. The signal readout circuit for an amperometric sensor as claimed in claim 7, wherein the compensation circuit comprises a second resistor and a capacitor connected in series.

9. A signal readout circuit for amperometric sensor, for reading out a readout signal of a sensor, wherein the sensor has a working electrode, a reference electrode, and a counter electrode, the readout circuit comprising:
    an amplifier, having a positive input end, a negative input end, and an output end, wherein the negative input end receives an input voltage, and the positive input end is connected to the reference electrode of the sensor;
    a first transistor, having a gate, a drain, and a source;
    a second transistor, having a gate, a drain, and a source, wherein the gates of the first transistor and the second transistor are connected to the output end of the amplifier;
    a third transistor, having a gate, a drain, and a source, connected to the first transistor and the counter electrode of the sensor; and
    a fourth transistor, having a gate, a drain, and a source, connected to the second transistor, wherein the gates of the third transistor and the fourth transistor are connected to the drains of the first transistor and the second transistor respectively; the drain of the third transistor is connected to the counter electrode of the sensor; and a first resistor is connected to the drain of the fourth transistor.

10. The signal readout circuit for an amperometric sensor as claimed in claim 9, wherein the amplifier is an operational transconductance amplifier.

11. The signal readout circuit for an amperometric sensor as claimed in claim 9, wherein the sources of the first transistor and the second transistor are connected to a power source, and the working electrode of the sensor is connected to a ground terminal.

12. The signal readout circuit for amperometric sensor as claimed in claim 11, further comprising a compensation circuit connected in parallel with the sensor.

13. The signal readout circuit for amperometric sensor as claimed in claim 12, wherein the compensation circuit comprises a second resistor and a capacitor connected in series.

14. The signal readout circuit for amperometric sensor as claimed in claim 9, wherein the sources of the first transistor and the second transistor are connected to a ground terminal, and the working electrode of the sensor is connected to a power source.

15. The signal readout circuit for amperometric sensor as claimed in claim 14, further comprising a compensation circuit connected with the sensor in parallel.

16. The signal readout circuit for amperometric sensor as claimed in claim 15, wherein the compensation circuit comprises a second resistor and a capacitor connected in series.

* * * * *